(12) United States Patent
Bigini (10) Patent No.: US 10,736,856 B2
(45) Date of Patent: Aug. 11, 2020

(54) USE OF XIBORNOL AS ACTIVE AGENT IN THE TREATMENT OF VIRAL INFECTIONS

(71) Applicant: ABIOGEN PHARMA S.P.A., Loc Ospedaletto, Pisa (IT)

(72) Inventor: Cristina Bigini, Loc. Ospedaletto (IT)

(73) Assignee: ABIOGEN PHARMA S.P.A., Ospedaletto, Pisa (IT)

( * ) Notice: Subject to any disclaimer, the term of this patent is extended or adjusted under 35 U.S.C. 154(b) by 0 days.

(21) Appl. No.: 16/315,322

(22) PCT Filed: Jul. 13, 2017

(86) PCT No.: PCT/IB2017/054247
§ 371 (c)(1),
(2) Date: Jan. 4, 2019

(87) PCT Pub. No.: WO2018/011751
PCT Pub. Date: Jan. 18, 2018

(65) Prior Publication Data
US 2019/0336456 A1 Nov. 7, 2019

(30) Foreign Application Priority Data
Jul. 15, 2016 (IT) .......................... 102016000074507

(51) Int. Cl.
*A61K 31/05* (2006.01)
*A61P 31/16* (2006.01)
*A61K 9/00* (2006.01)

(52) U.S. Cl.
CPC ............ *A61K 31/05* (2013.01); *A61K 9/0053* (2013.01); *A61P 31/16* (2018.01)

(58) Field of Classification Search
CPC ................................ A61P 31/12; A61P 31/20
See application file for complete search history.

(56) References Cited

PUBLICATIONS

Anonimo: "Bomilene torrinomedica", Nov. 14, 1997, retrieved from the Internet.
Cirri et al., Liquid spray formulations of xibomol by using self-microemulsifying drug delivery systems, International Journal of Pharmaceutics, vol. 340, No. 1-2, Jul. 19, 2007, pp. 84-91.
Herne N., "Essai comparatif en double aveugle randomise' xibornol, tetracycline et placebo dans les infections saisonnieres des voles aeriennes superiures", Medecines et Maladies Infectieuses, vol. 10, No. 3, Apr. 1980, pp. 185-190.
Scaglione F. et al., "Xibornol: multiple dose pharmacokinetics and diffusion in lung, tonsillar tissue and laryngeal mucosa", International Journal of Clinical Pharmacology Research, vol. 8, No. 6, Jan. 1, 1988, pp. 457-461.
Search Report and Written Opinion of PCT/IB2017/054247 dated Oct. 27, 2017.

*Primary Examiner* — San Ming R Hui
(74) *Attorney, Agent, or Firm* — Silvia Salvadori, P.C.; Silvia Salvadori (57) ABSTRACT

The use of xibornol as a virucidal agent is described in the prophylactic or therapeutic treatment of an infection caused by one or more viruses, said viruses comprising at least one of human Adenovirus, human Rhinovirus, human Coronavirus, and a combination thereof.

18 Claims, 3 Drawing Sheets

USE OF XIBORNOL AS ACTIVE AGENT IN THE TREATMENT OF VIRAL INFECTIONS

This application is a U.S. national stage of PCT/IB2017/054247 filed on 13 Jul. 2017, which claims priority to and the benefit of Italian Application No. 102016000074507 filed on 15 Jul. 2016, the contents of which are incorporated herein by reference in their entireties.

FIELD OF THE INVENTION

The present invention relates to the use of xibornol as an active agent in the treatment of viral infections caused by viruses, such as human Adenovirus, human Rhinovirus or human Coronavirus.

BACKGROUND ART

Respiratory infections are known to have a significant impact under the sanitary point of view, as they can cause hospitalization, and under the economic and social point of view, as they are responsible for a large investment in terms of health care resources, as well as for the direct costs of drug consumption and medical examinations, and for the indirect costs due to non-attendances at work and schools.

The frequency with which respiratory infections are found in people is very high, especially in case of sudden climate changes or in the presence of air pollution.

The extreme easiness of diffusion and contagion of these infections also means that they are often epidemic in nature, especially in the most vulnerable individuals such as the elderly and children, and recurrent, especially in immunosuppressed individuals.

The health care institute most affected by the problem is definitely the General Practitioner's outpatient Clinic, who is in the forefront to decide whether to turn to additional diagnostic tests or implement empirical treatment based on clinical, epidemiological and gravity criteria.

In a survey conducted in the United States in 1995, infections of the upper respiratory ways were the main cause of medical examination before the General Practitioner's and Emergency clinics, with 37 million medical examinations and 52% of patients with uncomplicated upper respiratory infections, treated with antibiotics according to the "National Ambulatory Medical Care Survey".

In fact, the most widely used method of treatment of these infections is exactly to make use of antibiotics, in most cases administered without a real and actual need, especially considering that these diseases have a complex aetiology due not only to the presence of bacteria, but often rather to the simultaneous presence of various other types of microorganisms, such as viruses and fungi.

Among the viruses that cause these infections, influenza virus, parainfluenza virus, human adenovirus, enterovirus, human rhinovirus, the Epstein-Barr virus, metapneumovirus, human coronarovirus, the respiratory syncytial virus, etc, can be mentioned.

In particular, human Adenovirus, human Rhinovirus and human Coronavirus are also known to cause diseases of various degrees at both respiratory and eye level, and in the pediatric population and in immunocompromised/immunosuppressed patients or patients suffering from other diseases, these viruses can sometimes lead to quite serious infections.

Under the therapeutic profile, unfortunately, there are no specific therapies to date for the treatment of each of these viruses, but rather generic symptomatic therapies and certain drugs, often steroids, for the more severe cases.

In general, however, the most widely used method of treatment of these infections is exactly to make use of antibiotics, in most cases administered without an effective necessity considering their inactivity on viruses, which are pathogens often prevailing in said pathologies, and whose abuse has also led today to the serious problem of bacterial resistance, which is so much discussed.

Therefore, in order to prevent the onset of phenomena of resistance to antibiotics, therapeutic alternatives have also been investigated, which provide for the use of oral antiseptics such as mouthwashes or tablets, based on chlorhexidine or benzydamine hydrochloride, or NSAIDs such as flurbiprofen, or other molecules with similar properties.

In fact, as said, they are symptomatic, which act on the painful symptom without resolving the cause underlying the same, associated to the simultaneous presence of one or more pathogens, also viral, among which often exactly human Adenovirus, human Rhinovirus and human Coronavirus.

The need to identify molecules having a remarkable virucidal activity, in particular against said viruses, is therefore still felt.

The object of the present invention therefore is to find an effective remedy against human Adenovirus, human Rhinovirus and human Coronavirus, which it is also well tolerated by the body.

SUMMARY OF THE INVENTION

Said object is achieved by the use of xibornol as a virucidal agent in the prophylactic or therapeutic treatment of an infection caused by one or more viruses, said viruses comprising at least one of human Adenovirus, human Rhinovirus, human Coronavirus, and a combination thereof, as set forth in claim 1.

According to another aspect, the present invention relates to a virucidal pharmaceutical composition comprising xibornol and suitable pharmaceutically acceptable excipients, for use in the prophylactic or therapeutic treatment of an infection caused by one or more viruses, said viruses comprising at least one of human Adenovirus, human Rhinovirus, human Coronavirus, and a combination thereof, as set forth in claim 10.

BRIEF DESCRIPTION OF THE FIGURES

The features and the advantages of the present invention will appear more clearly from the following detailed description, from the embodiments shown by way of non-limiting examples and from the accompanying figures, wherein.

DETAILED DESCRIPTION OF THE INVENTION

The invention therefore relates to the use of xibornol as a virucidal agent in the prophylactic or therapeutic treatment of an infection caused by one or more viruses, said viruses comprising at least one of human Adenovirus, human Rhinovirus, human Coronavirus, and a combination thereof.

As mentioned, human Adenovirus, human Rhinovirus and human Coronavirus are known to cause diseases of various degrees, depending also on age, on the specific health status, as well as on the immunological status of an individual.

Examples of said pathologies are cold diseases and diseases of the oral cavity and upper respiratory ways, such as acute and chronic tonsillitis, pharyngitis, laryngitis, nasopharyngitis and angina, but also, in certain cases, more complex diseases, such as febrile acute respiratory disease in children, acute respiratory infection (ARI), conjunctivitis, laryngotracheitis, pneumonia, acute follicular conjunctivitis, epidemic keratoconjunctivitis (EKC), acute pharyngoconjunctival fever (PCF), bronchitis, chronic bronchitis, infantile gastroenteritis, diseases of the gastrointestinal tract, diseases of the genitourinary tract (acute haemorrhagic cystitis), diseases of the nervous system (meningitis, encephalitis), disseminated infection (immunocompromised and immunocompetent children, transplanted adults), severe acute respiratory syndrome (SARS), laryngotracheobronchitis (Croup), bronchiolitis, community-acquired pneumonia (in hospitalized children). These viruses can also eventually result in the exacerbation of chronic lung diseases such as asthma, chronic obstructive pulmonary disease (COPD) and cystic fibrosis.

Xibornol or 6-isobornyl-3,4-xylenol, IUPAC name 4,5-dimethyl-2-[1,7,7-trimethylbicyclo[2.2.1]heptan-2-yl]phenol, is a phenol derivative of bornane, having the formula:

As will be apparent also from the examples given below, xibornol has been shown to act as a virucidal agent against human Adenovirus, human Rhinovirus or human Coronavirus, being able to significantly reduce the viral titer and cause a substantial viral reduction.

In particular, xibornol can therefore be effectively used as a virucidal agent for use in the prophylactic or therapeutic treatment of infection caused by one or more viruses, said viruses comprising at least one among human Adenovirus, human Rhinovirus, human Coronavirus, and a combination thereof, such as typically colds, diseases of the oral cavity and upper respiratory ways, such as tonsillitis, pharyngitis, laryngitis and angina. Preferably, said human Adenovirus is human Adenovirus 5.

Therefore, preferably, xibornol may be used as a virucidal agent in the prophylactic or therapeutic treatment of patients suffering from infections caused by one or more viruses, said viruses comprising at least one of human Adenovirus, human Rhinovirus, human Coronavirus, and a combination thereof.

More preferably, xibornol may be used as a virucidal agent in the prophylactic or therapeutic treatment of patients suffering from cold, disorders of the oral cavity or disorders of the upper respiratory ways caused by one or more viruses, said viruses comprising at least one of human Adenovirus, human Rhinovirus, human Coronavirus, and a combination thereof.

For the purposes of the present invention, the term "xibornol" is meant to include all optical isomers, geometric isomers and stereoisomers of 4,5-dimethyl-2-[(1,7,7-trimethylbicyclo[2.2.1]heptan-2-yl]phenol, as well as mixtures thereof, such as mixtures of enantiomers, racemic mixtures and mixtures of diastereomers, as well as all polymorphic forms thereof, both amorphous and crystalline, as well as co-crystalline, as well as anhydrous, hydrated and solvate forms, pharmaceutically acceptable salts, and mixtures thereof.

In a preferred embodiment of the invention, xibornol is 4,5-dimethyl-2-[(1 S,2R,4R)-1,7,7-trimethylbicyclo[2.2.1]heptan-2-yl]phenol or 4,5-dimethyl-2-[(1R,2S,4S)-1,7,7-trimethylbicyclo[2.2.1]heptan-2-yl]phenol.

The two single stereoisomers may be obtained by conventional enantiomeric separation techniques; in the examples given below, they have been obtained by chromatographic separation using a Chiralpak AD-H chiral column, 250×20 mm, 5 μm and using a mixture of n-hexane/isopropanol 90:10 as eluent.

In another preferred embodiment of the invention, xibornol is a mixture of 4,5-dimethyl-2-[(1S,2R,4R)-1,7,7-trimethylbicyclo[2.2.1]heptan-2-yl]phenol and 4,5-dimethyl-2-[(1R,2S,4S)-1,7,7-trimethylbicyclo[2.2.1]heptan-2-yl]phenol.

In yet another preferred embodiment of the invention, xibornol is a racemic mixture of 4,5-dimethyl-2-[(1 S,2R,4R)-1,7,7-trimethylbicyclo[2.2.1]heptan-2-yl]phenol and 4,5-dimethyl-2-[(1R,2S,4S)-1,7,7-trimethylbicyclo[2.2.1]heptan-2-yl]phenol.

Said xibornol may be administered via oral, nasal, intranasal, sublingual, buccal, intramuscular, intravenous, transdermal, sub-cutaneous, topical, rectal, or ocular route of administration.

Preferably, said xibornol is to be administered via oral route of administration.

In particularly preferred embodiments, xibornol is to be administered via oral route of administration in a dose of 15-56 mg per day, more preferably 18-48 mg per day, even more preferably in a dose of 24-36 mg per day.

For the purposes of the present invention, the term "day" means a period of 24±2 hours. In other preferred embodiments, xibornol is in the form of a unit dose comprising up to 10 mg of xibornol, preferably 4-8 mg of xibornol, more preferably 5-7 mg of xibornol, even more preferably 6 mg of xibornol.

Preferably, said unit dose is to be administered 3-8 times a day, more preferably 4-6 times a day, each time comprising the administration of 1-9 unit doses, preferably 1-5 unit doses, more preferably 1-2 unit doses, even more preferably one unit dose.

In another aspect, the present invention relates to a virucidal pharmaceutical composition comprising xibornol and suitable pharmaceutically acceptable excipients, for use in the prophylactic or therapeutic treatment of an infection caused by one or more viruses, said viruses comprising at least one of human Adenovirus, human Rhinovirus, human Coronavirus, and a combination thereof.

Preferably, said human Adenovirus is human Adenovirus 5.

The virucidal pharmaceutical composition comprising xibornol and pharmaceutically acceptable carriers can therefore be used for the therapeutic or prophylactic treatment of colds and infections of the mouth and the upper respiratory ways, such as acute and chronic tonsillitis, pharyngitis, laryngitis, nasopharyngitis and anginas, where angina means inflammation affecting the upper tract of the pharynx, jaws, tonsils and the soft palate.

Preferably, said virucidal pharmaceutical composition comprising xibornol and pharmaceutically acceptable carriers can therefore be used for the prophylactic or therapeutic treatment of colds, infections of the mouth and the upper respiratory ways, preferably for use in the therapeutic or prophylactic treatment of tonsillitis, pharyngitis, laryngitis and anginas.

In some embodiments, said virucidal pharmaceutical composition comprises 4,5-dimethyl-2-[(1S,2R,4R)-1,7,7-trimethylbicyclo[2.2.1]heptan-2-yl]phenol or 4,5-dimethyl-2-[(1R,2S,4S)-1,7,7-trimethylbicyclo[2.2.1]heptan-2-yl]phenol.

In other embodiments of the invention, said virucidal pharmaceutical composition comprises a mixture of 4,5-dimethyl-2-[(1 S,2R,4R)-1,7,7-trimethylbicyclo[2.2.1]heptan-2-yl]phenol and 4,5-dimethyl-2-[(1R,2S,4S)-1,7,7-trimethylbicyclo[2.2.1]heptan-2-yl]phenol.

In further embodiments of the invention, said virucidal pharmaceutical composition comprises a racemic mixture of 4,5-dimethyl-2-[(1S,2R,4R)-1,7,7-trimethylbicyclo [2.2.1] heptan-2-yl]phenol and 4,5-dimethyl-2-[(1R,2S,4S)-1,7,7-trimethylbicyclo[2.2.1]heptan-2-yl]phenol.

Said pharmaceutical composition may be a mouthwash, spray, orodispersible solid preparation, chewing gum, syrup, candy, gel, paste, eye drops, capsule, micro-capsule, tablet, mini-tablet, micro-tablet, pellet, multiparticulate, micronized particulate, pill, powder, granule, micro-granule, suppository, lotion, ointment, tincture, or cream.

In preferred embodiments, said pharmaceutical composition comprises up to 10 g of xibornol, more preferably 1-7 g of xibornol, even more preferably 3 g of xibornol.

Alternatively, it comprises up to 15% by weight xibornol with respect to the volume of the final pharmaceutical composition, more preferably up to 10% by weight with respect to the volume of the final pharmaceutical composition, even more preferably up to 3% by weight with respect to the volume of the final pharmaceutical composition.

In other preferred embodiments, said pharmaceutical composition is to be administered in unit doses comprising up to 10 mg of xibornol, preferably 4-8 mg of xibornol, more preferably 5-7 mg of xibornol, even more preferably 6 mg of xibornol.

Preferably, said unit doses of pharmaceutical composition are to be administered 3-8 times a day, more preferably 4-6 times a day, each time comprising the administration of 1-9 unit doses, preferably 1-5 unit doses, more preferably 1-2 unit doses, even more preferably one unit dose.

The pharmaceutical composition may be administered via oral, nasal, intra-nasal, sublingual, buccal, intramuscular, intravenous, transdermal, sub-cutaneous, topical, rectal, or ocular route of administration.

Preferably, said pharmaceutical composition is to be administered via oral route of administration.

In preferred embodiments, said pharmaceutical composition is to be administered via oral route of administration in the form of a solution, suspension or emulsion.

In even more preferred embodiments, said pharmaceutical composition in the form of a solution, suspension or emulsion is dispensed as a spray or mouthwash.

Preferably, said pharmaceutical composition in solution, suspension or emulsion, preferably dispensed as a spray or mouthwash, comprises up to 10 g of xibornol, more preferably 1-7 g of xibornol, even more preferably 3 g of xibornol.

Alternatively, said solution, suspension or emulsion, preferably dispensed as a spray or mouthwash, comprises up to 10 g xibornol per 100 mL of final solution, suspension or emulsion, more preferably 1-7 g xibornol per 100 mL of final solution, suspension or emulsion, even more preferably 3 g xibornol per 100 mL of final solution, suspension or emulsion.

In particularly preferred embodiments, said pharmaceutical composition is to be administered via oral route of administration in the form of a suspension dispensed as a spray.

In particularly preferred embodiments, the pharmaceutical composition to be administered via oral route of administration is in the form of a suspension dispensed as a spray comprising up to 10 g xibornol, more preferably 1-7 g xibornol, even more preferably 3 g xibornol, per 100 mL of pharmaceutical composition.

In even more preferred embodiments, the pharmaceutical composition is in the form of a suspension dispensed as a spray comprising up to 10 g xibornol, more preferably 1-7 g xibornol, even more preferably 3 g xibornol per 100 mL of pharmaceutical composition, said pharmaceutical composition having to be administered via oral route of administration in unit doses comprising up to 10 mg xibornol, preferably 4-8 mg xibornol, more preferably 5-7 mg xibornol, even more preferably 6 mg xibornol; preferably, said unit doses are to be administered 3-8 times a day, more preferably 4-6 times a day, each time comprising the administration of 1-9 unit doses, preferably 1-5 unit doses, more preferably 1-2 unit doses, even more preferably one unit dose.

Particularly preferred is the pharmaceutical composition in the form of a suspension, dispensed as a spray, comprising 3 g of xibornol per 100 mL of the pharmaceutical composition, to be administered via oral route of administration 4-6 times a day.

In other embodiments, said pharmaceutical composition is in a solid form, such as an orodispersible solid preparation, chewing-gum, candy, capsule, micro-capsule, tablet, mini-tablet, micro-tablet, pellet, multiparticulate, micronized particles, pill, powder, granule, microgranule or suppository.

Preferably, said pharmaceutical composition is in solid form comprising up to 600 mg xibornol.

The pharmaceutical composition may further comprise pharmaceutically acceptable carriers.

Suitable pharmaceutically acceptable carriers are for example pH adjusters, isotonicity adjusters, stabilizers, chelating agents, preservatives, thickeners, emulsifying agents, antioxidants, solvents, co-solvents and flavours.

Preferred PH adjusters are citric acid, sodium citrate, sodium acetate, boric acid, sodium borate, sodium bicarbonate, phosphoric acid and salts thereof, even more preferably citric acid and sodium citrate (citrate buffer) and sodium bicarbonate.

Among isotonicity adjusters, sodium chloride is preferred.

Among stabilizers, mannitol, dextran or mixtures thereof are preferred.

Among chelating agents, EDTA or a salt thereof, such as sodium EDTA, is preferred.

Among preservatives, benzyl alcohol, methyl paraben and propyl paraben, sorbic acid and salts thereof are preferred.

Among thickeners, methylcellulose, hydroxyethylcellulose, hydroxypropyl cellulose, sodium carboxymethylcellulose, sodium alginate and polyvinylpyrrolidone are preferred.

Among the emulsifying agents, sodium dodecyl sulfate and polysorbates are preferred.

Among antioxidants, sodium metabisulphite, potassium metabisulphite, sodium sulphite, butylated hydroxy anisole (BHA), butylated hydroxy toluene (BHT), ascorbic acid and sodium ascorbate are preferred.

Among the solvents, water is preferred.

Among the co-solvents, alcohols such as ethanol, glycols such as diethylenglycol monoethylether, and glycerin are preferred.

Other pharmaceutically acceptable carriers are for example natural starch, partially hydrolyzed starch, lactose, glucose, sucrose, sodium saccharine, mannitol, sorbitol, caprylocaproyl polyoxyl-8 glyceride, cellulose and derivatives thereof, microcrystalline cellulose and derivatives thereof, sodium carboxymethylcellulose, calcium phosphate, calcium carbonate, calcium sulfate, magnesium stearate, maltodextrin, gelatin, gum tragacanth, arabic gum, xanthan gum, talc, silica, colloidal silica, precipitated silica, magnesium silicates, aluminum silicates, sodium lauryl sulfate, magnesium lauryl sulfate, methacrylate copolymers, and mixtures thereof.

All pharmaceutical compositions described above can be prepared by using methods known in the art according to the route of administration.

It should be understood that all the aspects identified as preferred and advantageous for the use of xibornol are deemed to be similarly preferred and advantageous also for the pharmaceutical compositions, the unit doses and their respective uses in the treatment of the viral infections described above.

All combinations of the preferred aspects of the use of xibornol, the pharmaceutical composition, the unit doses and the respective uses in the treatment of the viral infections described above are to be understood as herein described.

Below are working examples of the present invention provided for illustrative purposes.

EXAMPLES

Example 1—Xibornol Virucidal Efficacy Tests

The experimentation was conducted by using the following strains from ATCC:
- VR-5 Human Adenovirus 5; Strain: Adenoid 75,
- VR-286 Picornaviridae, Rhinovirus, Human Rhinovirus A,
- VR-740 Human Coronavirus.

The cell lines used for the isolation of the target viruses were:
- ATCC CCL-2 HeLa—Cervical Adenocarcinoma—Human (*Homo sapiens*), briefly 'HeLa', for the study of Human Adenovirus 5 and Human Rhinovirus, and
- ATCC CCL-171 MRC-5-Lung Fibroblast-Human (*Homo Sapiens*), briefly 'MRC-5' for the study of Human Coronavirus.

The tests to assess the toxicity of xibornol were performed as per UNI EN 14476 protocol, which refers to the "virucidal activity of chemical disinfectants or antiseptics for tools, surfaces or hands forming a physically stable homogeneous mixture when diluted with hard water or water", suitably adapted, also considering that xibornol is soluble in alcohol (ethanol) that is already well known to have toxic effects for cell cultures.

Therefore, it was decided to use preparations in which xibornol was diluted with different solvents, in order also to be able to test both the solution and the suspension condition. After several tests, a reliable method was set up, by using Labrasol®, namely caprylocaproyl polyoxyl-8 glyceride, as solvent and formulating xibornol in solution.

Virucidal Activity Laboratory Tests

For each of the 3 viruses, 3 replicates were performed with 10 mL mixtures consisting of:
- 1 mL Labrasol® ("clean" tests) or 1 mL of fetal bovine serum ("dirt" tests);
- 8 mL xibornol for each dilution (8%, 3%, 0.5%) at the non-toxic concentration for the cell cultures: $10^{-3}$, $10^{-2}$ and $10^{-1}$ respectively, and corresponding to 0.008 g/100 mL, 0.030 g/100 mL and 0.05 g/100 mL. Dilutions made in Labrasol®;
- 1 mL of virus with known titer.

The tests carried out in "dirt" situations, specified by the standard protocol, were intended to create a more "difficult" environment for the performance of the virucidal activity by xibornol, hindered in its activity by the presence of further polluting components, as actually happens in the application environment of the active ingredient, allowing recreating and simulating as closely as possible the conditions of use.

For tests performed in "dirt" condition, the erythrocytes were not mixed with the bovine fetal serum, as indicated by the European standard, because of the interfering effect they have towards the cell lines used in the tests, which would have led to difficulties in interpreting the results.

Moreover, for each replicate, a negative control was used, consisting of:
- 1 mL virus;
- 9 mL Labrasol® ("clean" tests) or 8 mL Labrasol®+1 mL fetal bovine serum ("dirt" tests).

Contact time: 15 minutes.

After this interval, the mixtures were analysed to assess the residual viral titer by titration, Karber micromethod.

Statistical Analysis

The data obtained were analysed with the Excel program for the evaluation of averages and total logarithmic standard deviations.

Results

The results are shown in the following tables 1-6 and are subdivided by virus and type of test ("clean"/"dirt").

1. Human Adenovirus 5

TABLE 1

"Clean" data (average total values)

| | Dilution used | Working concentrations (g/100 mL) | Average viral titre after 15 minutes contact (Log DCP50/mL ± DS) | Logarithmic reduction |
|---|---|---|---|---|
| Positive control | | | 4.40 ± 0.1 | |
| 8% xibornol solution | $10^{-3}$ | 0.008 | 2 ± 0.8 | 2.4 |
| 3% xibornol solution | $10^{-2}$ | 0.03 | 1.3 ± 1 | 3.1 |
| 0.5% xibornol solution | $10^{-1}$ | 0.05 | 1.1 ± 0.1 | 3.3 |

TABLE 2

"Dirt" data (average total values)

| | Dilution used | Working concentrations (g/100 mL) | Average viral titre after 15 minutes contact (Log DCP50/mL ± DS) | Logarithmic reduction |
|---|---|---|---|---|
| Positive control | | | 3.1 ± 0.2 | |
| 8% xibornol solution | $10^{-3}$ | 0.008 | 1.1 ± 0.6 | 2 |
| 3% xibornol solution | $10^{-2}$ | 0.03 | 1.2 ± 0.6 | 1.9 |
| 0.5% xibornol solution | $10^{-1}$ | 0.05 | 0.8 ± 0.5 | 2.3 |

2. Human Coronavirus

TABLE 3

"Clean" data (average total values)

| | Dilution used | Working concentrations (g/100 mL) | Average viral titre after 15 minutes contact (Log DCP50/mL ± DS) | Logarithmic reduction |
|---|---|---|---|---|
| Positive control | | | 5.2 ± 0.2 | |
| 8% xibornol solution | $10^{-3}$ | 0.008 | 1.8 ± 0.7 | 3.4 |
| 3% xibornol solution | $10^{-2}$ | 0.03 | 1.4 ± 0 | 3.8 |
| 0.5% xibornol solution | $10^{-1}$ | 0.05 | 1.6 ± 0.3 | 3.6 |

TABLE 4

"Dirt" data (average total values)

| | Dilution used | Working concentrations (g/100 mL) | Average viral titre after 15 minutes contact (Log DCP50/mL ± DS) | Logarithmic reduction |
|---|---|---|---|---|
| Positive control | | | 4.1 ± 0.2 | |
| 8% xibornol solution | $10^{-3}$ | 0.008 | 1.7 ± 0.7 | 2.3 |
| 3% xibornol solution | $10^{-2}$ | 0.03 | 1.5 ± 0.6 | 2.6 |
| 0.5% xibornol solution | $10^{-1}$ | 0.05 | 1.6 ± 0.4 | 2.5 |

3. Human Rhinovirus

TABLE 5

"Clean" data (average total values)

| | Dilution used | Working concentrations (g/100 mL) | Average viral titre after 15 minutes contact (Log DCP50/mL ± DS) | Logarithmic reduction |
|---|---|---|---|---|
| Positive control | | | 4.2 ± 0.3 | |
| 8% xibornol solution | $10^{-3}$ | 0.008 | 2 ± 0.1 | 2.2 |
| 3% xibornol solution | $10^{-2}$ | 0.03 | 1.3 ± 0.5 | 2.9 |
| 0.5% xibornol solution | $10^{-1}$ | 0.05 | 1.2 ± 0.4 | 3 |

TABLE 6

"Dirt" data (average total values)

| | Dilution used | Working concentrations (g/100 mL) | Average viral titre after 15 minutes contact (Log DCP50/mL ± DS) | Logarithmic reduction |
|---|---|---|---|---|
| Positive control | | | 3.8 ± 0.1 | |
| 8% xibornol solution | $10^{-3}$ | 0.008 | 1 ± 0.1 | 2.8 |
| 3% xibornol solution | $10^{-2}$ | 0.03 | 0.7 ± 0.1 | 3.1 |
| 0.5% xibornol solution | $10^{-1}$ | 0.05 | 0.8 ± 0.1 | 3 |

The results, though preliminary and obtained from a small number of samples, show beyond any doubt the high efficacy of xibornol in reducing the viral load already after 15 minutes of contact, with a killing extent greater than about 2 orders of magnitude on each virus tested and at all concentrations tested, and with killing peaks which reach even the value of 3.8 orders of magnitude in the case of efficacy tests conducted on Human Coronavirus. It should be considered that such significant results in terms of reduction of the viral load are obtained respectively at concentration values of xibornol of 0.008 g/100 mL, 0.030 g/100 mL and 0.05 g/100 mL, which are considered quite low concentration values.

It should also be noted that such an effectiveness increases noticeably with increasing concentration of xibornol.

It should also be noted that said effectiveness is widely demonstrated also in the case of tests carried out in worsening conditions, i.e. in tests marked "dirt", where, despite the presence of an environment that is more hostile to the virucidal agent, the reduction of the viral titer has demonstrated an average of more than two orders of magnitude, reaching and exceeding the value of 3 orders of magnitude reduction in the case of human Rhinovirus.

Figure 1:
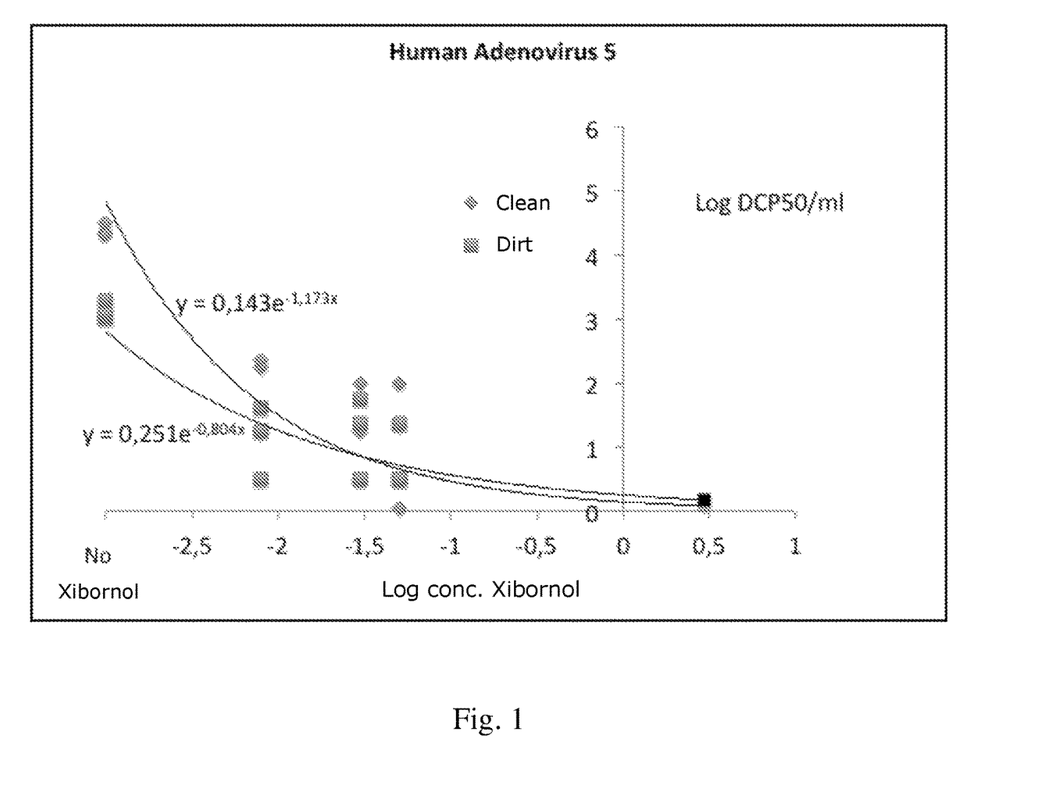
FIG. 1 shows the trend of the viral titer for Human Adenovirus 5 obtained with the solutions of Example 1.
Figure 2:
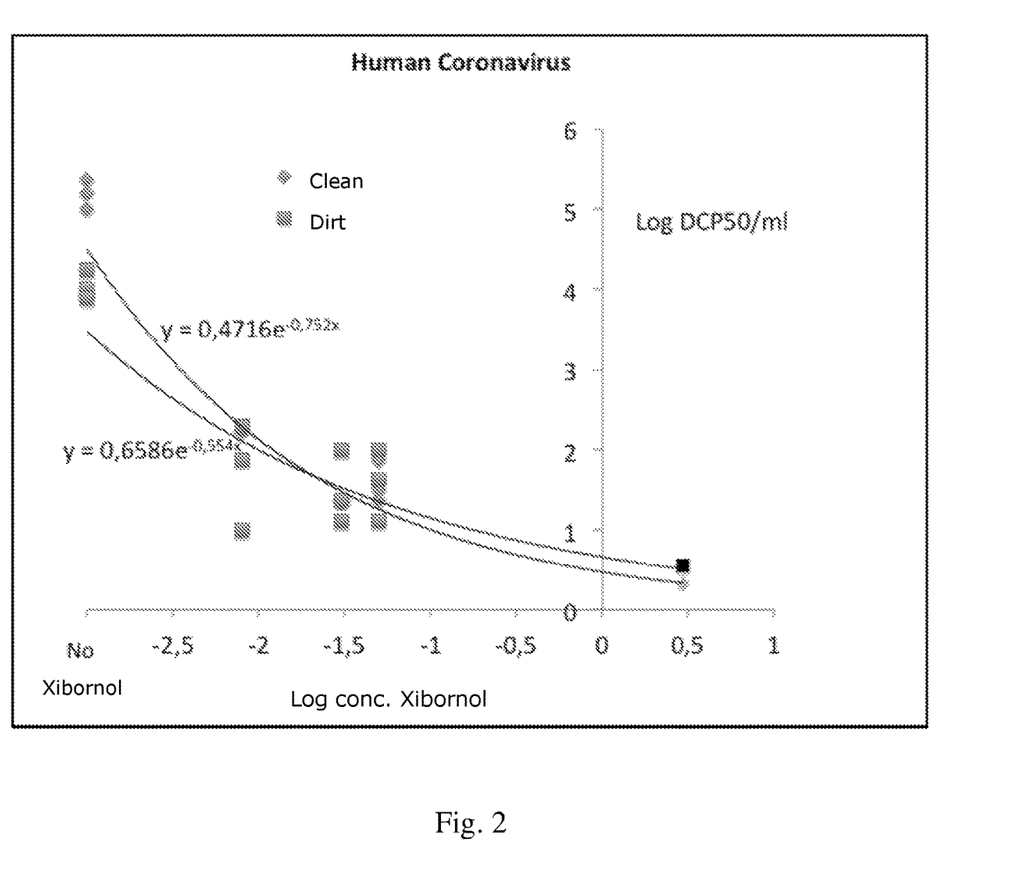
FIG. 2 shows the trend of the viral titer for Human Coronavirus obtained with the solutions of Example 1.
Figure 3:
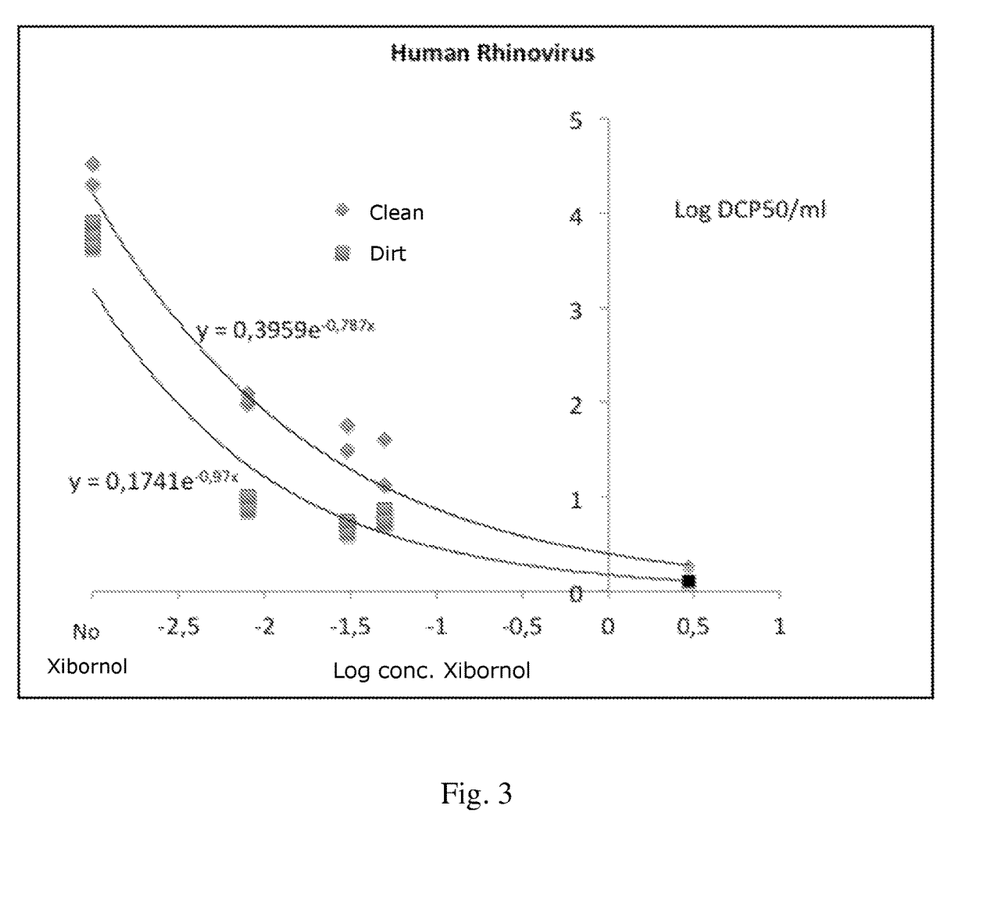
FIG. 3 shows the trend of the viral titer for Human Rhinovirus obtained with the solutions of Example 1.

The data obtained were also processed graphically in FIGS. 1-3, which show the trend curves of the titer of viral loads for the three viruses tested respectively, where the abscissa shows the logarithm of the working concentrations of xibornol (expressed in g per 100 mL of solution) and the ordinate shows the logarithm of the 50% cytopathogenic dose per mL virus.

In particular, the equations of the curves were obtained, representing in an optimal manner the trend of these experimental data and making possible to extrapolate the viral concentration for greater concentrations of xibornol than used in the tests, highlighting in particular that, at the concentration corresponding to 3 g per 100 mL of solution, the reduction of the viral load titer (expressed as logarithm) for all viruses considered, is at least of two orders of magnitude, with a final average titer after treatment very close to zero.

The above tests therefore allowed evaluating and demonstrating the virucidal efficacy of the active ingredient xibornol; in particular, they allowed demonstrating the almost total reduction of the viral titer for all viruses considered at a concentration of xibornol of 3 g per 100 mL of solution.

Xibornol can therefore be effectively used as a virucidal agent for use in the prophylactic or therapeutic treatment of infection caused by human Adenovirus, preferably human Adenovirus 5, human Rhinovirus, human Coronavirus, or a combination thereof, such as typically colds, diseases of the oral cavity and upper respiratory ways, such as tonsillitis, pharyngitis, and laryngitis.

Example 2—Preparation of a Pharmaceutical Composition in the Form of a Spray Suspension Comprising Xibornol 100 mL of a spray suspension were prepared by admixing 2.0 g xibornol in the form of a racemic mixture of 4,5-dimethyl-2-[(1 S,2R,4R)-1,7,7-trimethylbicyclo[2.2.1]heptan-2-yl]phenol and 4,5-dimethyl-2-[(1R,2S,4S)-1,7,7-trimethylbicyclo[2.2.1]heptan-2-yl]phenol with the excipients indicated in the following table 7:

| Excipients | (weight/volume) |
|---|---|
| Glycerol | 8.0 g |
| Dispersible cellulose | 3.0 g |
| Diethylene glycol monoethylether | 3.0 g |
| Simethicone in 30% emulsion | 2.0 g |
| Propyl and methyl paraben | 0.400 g |
| Sodium saccharine | 0.500 g |
| Colloidal anhydrous silica | 0.200 g |
| Polyethoxylated castor oil | 0.200 g |
| Potassium sorbate | 0.100 g |
| Purified water as needed | to 100 mL |

The suspension thus prepared was stable and effective as virucidal suspension in the treatment of infections caused by one or more viruses, such as Human Adenovirus, Human Rhinovirus, Human Coronavirus and combinations thereof.

Example 3—Preparation of a Pharmaceutical Composition in the Form of a Spray Suspension Comprising Xibornol 100 mL of a spray suspension were prepared by admixing 3.0 g xibornol in the form of a racemic mixture of 4,5-dimethyl-2-[(1 S,2R,4R)-1,7,7-trimethylbicyclo[2.2.1]heptan-2-yl]phenol and 4,5-dimethyl-2-[(1R,2S,4S)-1,7,7-trimethylbicyclo[2.2.1]heptan-2-yl]phenol with the excipients indicated in the following table 8:

| Excipients | (weight/volume) |
|---|---|
| Glycerol | 7.0 g |
| Cellulose | 2.0 g |
| Diethylene glycol monoethylether | 2.0 g |
| Xanthan gum | 1.0 g |
| Ethanol 96% (v/v) | 1.0 g |
| Simethicone in 30% emulsion | 2.0 g |
| Sodium saccharine | 0.400 g |
| Colloidal anhydrous silica | 0.200 g |
| Polyethoxylated castor oil | 0.200 g |
| Potassium sorbate | 0.100 g |
| Purified water as needed | to 100 mL |

The suspension thus prepared was stable and effective as virucidal suspension in the treatment of infections caused by one or more viruses, such as Human Adenovirus, Human Rhinovirus, Human Coronavirus and combinations thereof.

Likewise, the pharmaceutical compositions comprising xibornol and pharmaceutically acceptable carriers can therefore be used for the prophylactic or therapeutic treatment of colds, infections of the mouth and the upper respiratory ways, preferably for use in the therapeutic or prophylactic treatment of tonsillitis, pharyngitis, laryngitis and anginas.

In other words, the experiments have shown that pharmaceutical compositions comprising xibornol and pharmaceutically acceptable carriers can be used in the prophylactic or therapeutic treatment of patients suffering from infections caused by one or more viruses, said viruses comprising at least one of human Adenovirus, human Rhinovirus, human Coronavirus, and a combination thereof. Specifically, the pharmaceutical compositions comprising xibornol and pharmaceutically acceptable carriers can be used for the prophylactic or therapeutic treatment of patients suffering from colds, infections of the mouth and the upper respiratory tract, such as tonsillitis, pharyngitis and laryngitis caused by such viruses.

The invention claimed is:

1. A method for the prophylactic or therapeutic treatment of an infection caused by one or more viruses, said viruses comprising at least one of human Adenovirus, human Rhinovirus, human Coronavirus, and a combination thereof, the method comprising the step of administering a therapeutically effective amount of xibornol, as a virucidal agent, to patients in need thereof.

2. The method of claim 1, wherein said human Adenovirus is human Adenovirus 5.

3. The method of claim 1, wherein said infection caused by one or more viruses is a cold, a disorder of the oral cavity or a disorder of the upper airways.

4. The method of claim 3, wherein said cold, disorder of the oral cavity or disorder of the upper airways is tonsillitis, pharyngitis, laryngitis or angina.

5. The method of claim 1, wherein said xibornol is to be administered via oral, nasal, intra-nasal, sublingual, buccal, intramuscular, intravenous, transdermal, sub-cutaneous, topical, rectal, or ocular route of administration.

6. The method of claim 5, wherein said xibornol is to be administered via oral route of administration.

7. The method of claim 6, wherein said xibornol is to be administered in a dose of 15-56 mg per day.

8. The method of claim 6, wherein said xibornol is in the form of a unit dose comprising up to 10 mg of xibornol.

9. The method of claim 8, wherein said unit dose is to be administered 3-8 times a day, each time comprising the administration of 1-9 unit doses.

10. The method of claim 1 comprising the step of administering a therapeutically effective amount of a virucidal pharmaceutical composition, comprising xibornol and pharmaceutically acceptable excipients, to patients in need thereof.

11. The method of claim 10, wherein the virucidal pharmaceutical composition is a mouthwash, spray, orodispersible solid preparation, chewing gum, syrup, candy, gel, paste, eye drops, capsule, micro-capsule, tablet, mini-tablet, micro-tablet, pellet, multiparticulate, micronized particulate, pill, powder, granule, micro-granule, suppository, lotion, ointment, tincture, or cream.

12. The method of claim 10, wherein said composition comprises up to 10 g of xibornol.

13. The method of claim 10, wherein said composition comprises xibornol up to 15% by weight with respect to the volume of the composition.

14. The method of claim 10, wherein said composition is to be administered in unit doses, each unit dose comprising up to 10 mg of xibornol.

15. The method of claim 10, wherein said unit doses of composition are to be administered 3-8 times a day, each time comprising the administration of 1-9 unit doses.

16. The method of claim 10, wherein said composition is to be administered via oral, nasal, intra-nasal, sublingual, buccal, intramuscular, intravenous, transdermal, sub-cutaneous, topical, rectal, or ocular route of administration.

17. The method of claim 10, wherein said composition is to be administered via oral route of administration, is in the form of a solution, suspension or emulsion, and comprises up to 10 g of xibornol, per 100 mL of the pharmaceutical composition.

18. The method of claim 1, wherein said composition is in the form of a suspension, to be dispensed as a spray, comprising 3 g of xibornol per 100 mL of the pharmaceutical composition, to be administered via oral route of administration 4-6 times a day.

\* \* \* \* \*